United States Patent
Williams, III et al.

(10) Patent No.: US 7,621,919 B2
(45) Date of Patent: Nov. 24, 2009

(54) ORTHOPEDIC CUTTING BLOCK

(75) Inventors: Philip F. Williams, III, Teaneck, NJ (US); Matthew E. Seelig, Upper Saddle River, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 89 days.

(21) Appl. No.: 10/820,928

(22) Filed: Apr. 8, 2004

(65) Prior Publication Data
US 2005/0228393 A1 Oct. 13, 2005

(51) Int. Cl.
*A61F 5/00* (2006.01)
(52) U.S. Cl. ........................................................ 606/87
(58) Field of Classification Search ................... 606/96, 606/87
See application file for complete search history.

(56) References Cited

U.S. PATENT DOCUMENTS

| | | | |
|---|---|---|---|
| 4,075,920 A * | 2/1978 | Neal | ........................... 83/745 |
| 4,567,885 A | 2/1986 | Androphy | |
| 5,454,816 A | 10/1995 | Ashby | |
| 5,749,876 A * | 5/1998 | Duvillier et al. | .............. 606/88 |
| 5,817,097 A | 10/1998 | Howard et al. | |
| 6,214,011 B1 | 4/2001 | Masini | |
| 6,258,095 B1 | 7/2001 | Lombardo et al. | |
| 6,393,958 B1 * | 5/2002 | Owens et al. | .................. 83/762 |
| 6,458,135 B1 | 10/2002 | Harwin et al. | |
| 6,558,391 B2 | 5/2003 | Axelson, Jr. et al. | |
| 6,602,259 B1 | 8/2003 | Masini | |
| 2004/0260301 A1 * | 12/2004 | Lionberger et al. | ........... 606/88 |

* cited by examiner

*Primary Examiner*—Corrine M McDermott
*Assistant Examiner*—Christopher D Prone
(74) *Attorney, Agent, or Firm*—Lerner, David, Littenberg, Krumholz & Mentlik, LLP

(57) ABSTRACT

An orthopedic cutting block for use in shaping a bone. The cutting block having at least two components, one of which is made of a polymeric material. The cutting block allowing for precise and accurate cuts to be made, while being inexpensive to manufacture and disposable after a single use.

7 Claims, 4 Drawing Sheets

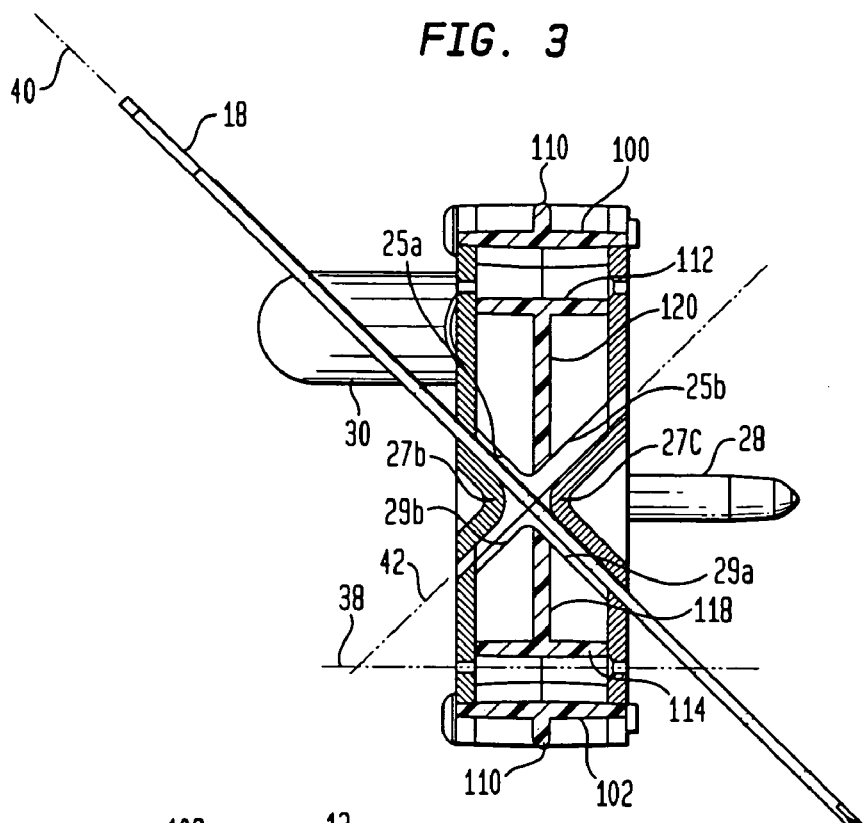
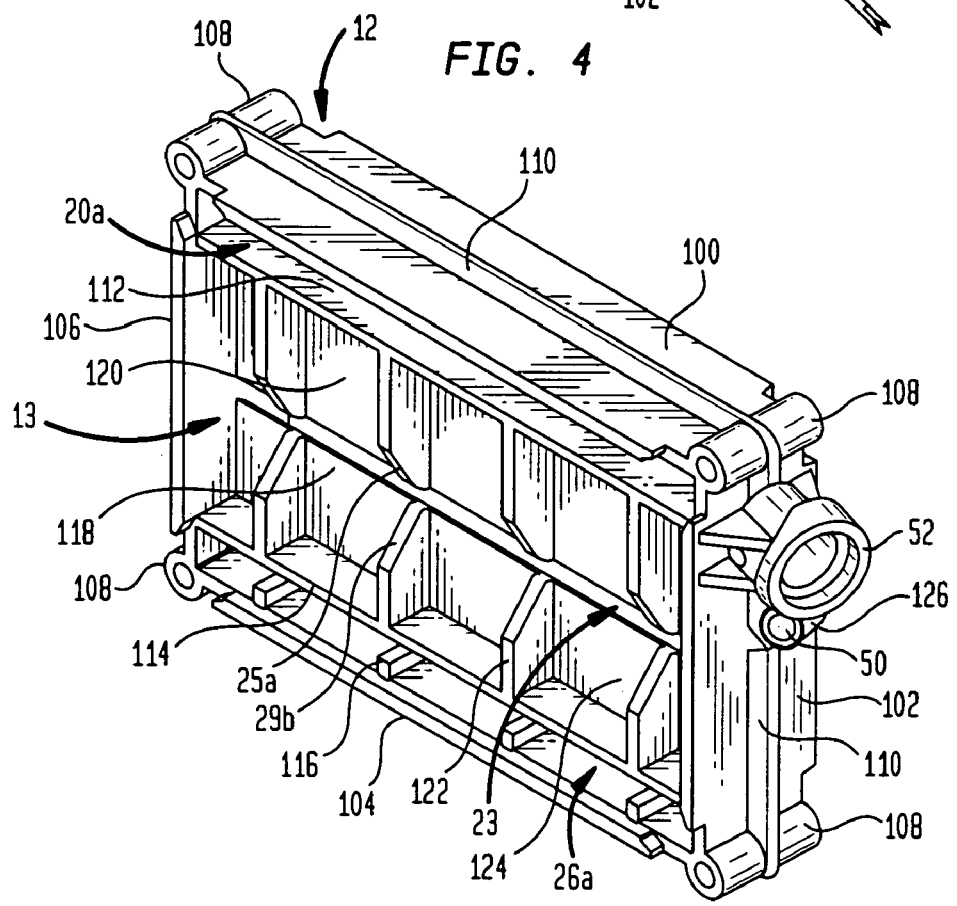

ORTHOPEDIC CUTTING BLOCK

FIELD OF THE INVENTION

The present invention relates to orthopedic cutting blocks for use in shaping a bone and, more particularly, to an orthopedic cutting block that has been designed to permit low-cost manufacturing methods while still maintaining the required accuracy of the cuts.

BACKGROUND OF THE INVENTION

Many surgical operations call for the precise and accurate cuts of bone material. Generally, these cuts, or resections, are made using surgical saws or milling devices. These instruments, while excellent at cutting the bone material, typically require cutting guides in surgical procedures calling for accurate cuts. For example, a surgeon performing a total knee arthroplasty must make several cuts on the distal end of the femur to properly fit a prosthetic femoral component. If these resections are incorrectly made, the surgery can result in failure and require further corrective procedures.

For this and other reasons, surgeons often employ the use of surgical cutting blocks, known also as cutting guides. These blocks aid in guiding the cutting device during the cutting of the bone material. A specific type of cutting block is one used to create four cuts on an already resected distal portion of the femur as part of a total knee replacement. These four cuts are the anterior and posterior cuts and the anterior and posterior chamfer cuts. Examples of these femoral cutting blocks are shown in U.S. Pat. No. 5,454,816 to Ashby, U.S. Pat. No. 6,258,095 to Lombardo et al., and U.S. Pat. No. 6,558,391 to Axelson, Jr. et al.

While cutting blocks such as those described above are useful in performing the various cuts on a bone, they have their drawbacks. Most importantly, the manufacturing costs associated with such blocks are often quite high. A standard block is typically constructed of metallic material machined from a solid block or from several solid metal pieces and assembled to allow for the various cuts to be performed. The high costs require these expensive cutting blocks to be utilized in multiple surgeries. This re-use requires the cleaning and sterilization of such a block before each use, which adds additional cost. Furthermore, multiple uses of a cutting block allows for greater chance of misaligning a cutting tool, such as a flat oscillating saw blade, due to wear of the cutting guide surfaces. Hence, a disposable single use cutting block would be advantageous. Therefore, there is a need for a cutting block that can be inexpensively manufactured, while maintaining the required precise and accurate dimensions needed for making cuts.

SUMMARY OF THE INVENTION

A first aspect of the present invention is a bone cutting block comprising a polymeric first body portion having at least one aperture extending therethrough for receiving a bone cutting tool and a non-polymeric second body portion having a cutting tool guide surface thereon, the second body portion coupled to the first body portion with the cutting tool guide surface thereon in communication with the aperture.

In some embodiments, the first body portion has a first external surface for facing a bone and second external surface for facing away from the bone with the second body portion coupled to one of the first or second surfaces. In other embodiments, the bone cutting block further comprises a non-polymeric third body portion coupled to the other of the external surfaces. In other embodiments, one of the first, second, or third body portions further comprises means for attaching to a bone surface. In other embodiments, the means for attaching to bone surface are pins. In certain embodiments, the third body portion has a cutting tool guide surface thereon in communication with the aperture of the first body portion and the cutting tool guide surface of the second body portion. In any of these embodiments, the second and third portion may be made of metal. In some embodiments, the first body portion further comprises four apertures and the second and third body portion further comprise four cutting tool guide surfaces respectively, groups of the apertures and the cutting tool guide surfaces in communication with one another to form four passages. The cutting tool guide surfaces of this embodiment may be slots.

Another embodiment of the present invention is an orthopedic cutting block for performing four cuts on the resected distal end of the femur. This block comprises a base portion having a first side, a second side, and three slots extending from the first side to the second side, a first guide portion having four slots extending through the first guide portion, and a second guide portion having four passages extending through the second guide portion. In this embodiment, the first guide portion is attached to the first side of the base portion, the second guide portion is attached to the second side of the base portion, and the three passages of the base portion, the slot on the first guide portion and the second guide portion align to form four passages extending through the cutting block. In this embodiment, the base portion may be made of polymer material and the first and second guide portions may be made of metal. Finally, the embodiment may further include means for attaching the cutting block to a bone surface, such as pins.

Another aspect of the present invention is a method for forming an orthopedic cutting block for guiding bone saws. This method comprising injection molding a polymeric body having passageways therein, placing first and second metal plates on respective first and second sides of the polymeric body, the plates having saw guides thereon, the placement including aligning the guides with the passageways, and coupling the first and second plates with the body therebetween.

BRIEF DESCRIPTION OF THE DRAWINGS

The present invention will be better understood on reading the following detailed description of non-limiting embodiments thereof, and on examining the accompanying drawings, in which:

FIG. 3 is a cross-sectional view of the apparatus according to an embodiment of the present invention as shown in FIG. 1;

FIG. 4 is a perspective view of a base portion according to an embodiment of the present invention;

DETAILED DESCRIPTION

Figure 1:
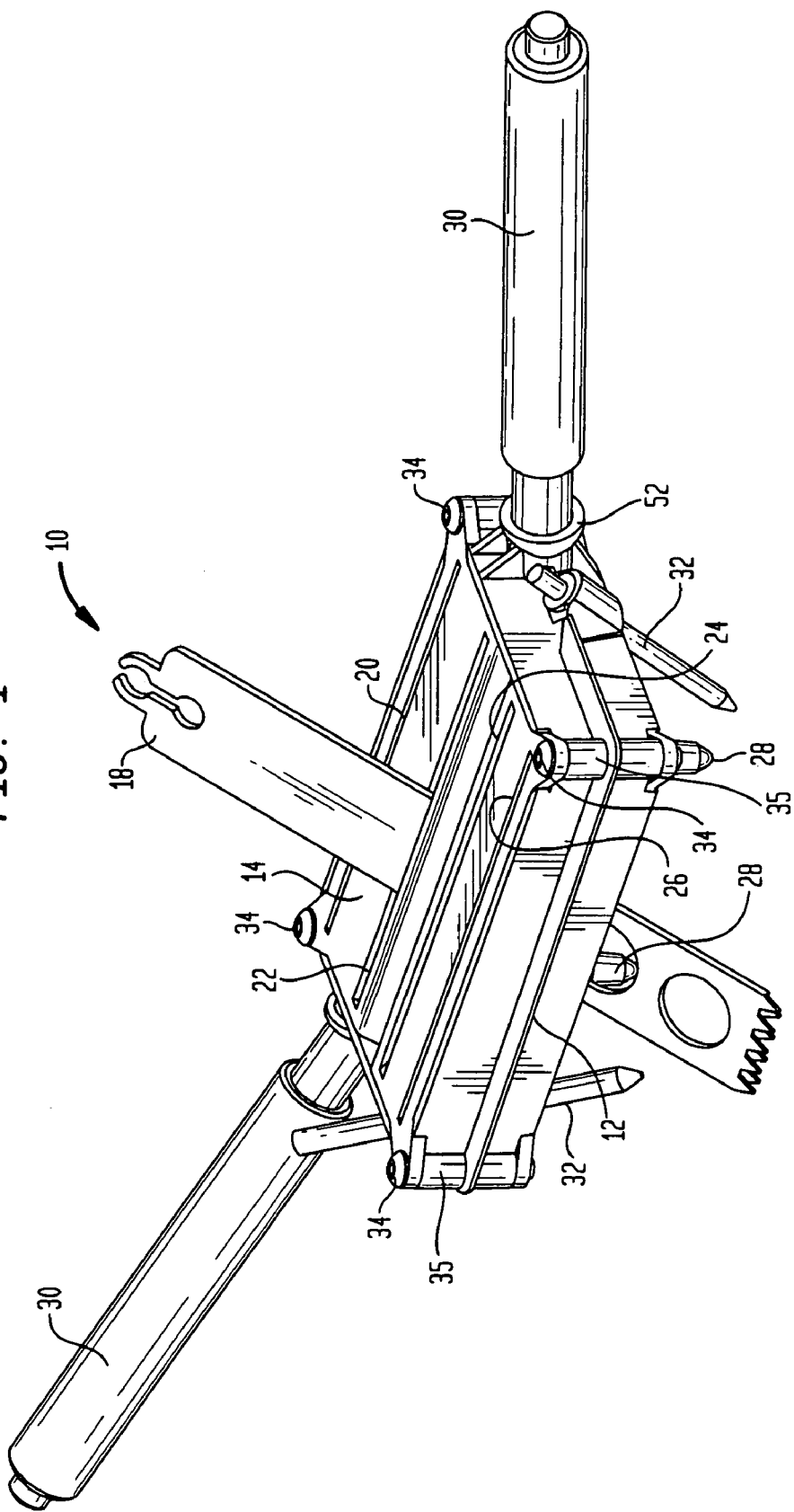
FIG. 1 is a perspective view of the apparatus according to an embodiment of the present invention for use in resecting a distal femur in its fully constructed form with a saw blade extending through a passage.

In describing the preferred embodiments of the subject matter illustrated and to be described with respect to the drawings, specific terminology will be resorted to for the sake of clarity. However, the invention is not intended to be limited to the specific term so selected, and is to be understood that each specific term includes all technical equivalence which operate in a similar manner to accomplish a similar purpose.

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Referring to the drawings, wherein like reference numerals represent like elements, there is shown in FIGS. 1-6, in accordance with embodiments of the present invention, a cutting guide, or cutting block, designated generally by reference numeral 10. In the preferred embodiment, cutting block 10 is designed to be used in resecting a distal femur and includes a base or first body portion 12, a first guide or second body portion 14, and a second guide or third body portion 16. The preferred embodiment of the present invention is a cutting block 10 used to make four cuts on the distal end of the femur, during a total knee arthroplasty, the anterior and posterior cuts and the anterior and posterior chamfer cuts subsequent to the distal cut being made. However, it should be noted that cutting block 10 could also have broad utility during any orthopedic procedure where a guide for a cutting instrument is required. For example, a cutting block using the technology used in cutting block 10 can be used during tibial preparation of a total knee arthroplasty. Cutting block 10 is shown in the figures along with oscillating saw blade 18. Saw blade 18 is used to perform the cutting, or resecting, of the bone surface. It should be noted that other devices for cutting, as known in the art, can also be utilized, such as reciprocating saws or milling cutters.

The base portion 12, as best shown in FIG. 4, is made of a polymeric material. In the preferred embodiment, the base portion is manufactured by an injection molding process from commercially available Ultem® polymer. However, it should be noted that other materials can be utilized. For example, it is contemplated that polypropylene or polycarbonate can also be used to manufacture base portion 12. Preferably, the material should be one that is easy to utilize in manufacturing the base portion 12, while also being relatively inexpensive.

In the preferred embodiment, base portion 12 is rectangularly shaped having rectangular faces 13 and an opposite face (not shown) and passages 20a, 23, and 26a extending therethrough. However, in other embodiments, base portion 12 can be other shapes and can include any number of passages therethrough. For example, a base portion 12 including only one passage can be utilized in preparing the proximal end of the tibia during a total knee arthroplasty. In the preferred embodiment, passages 20a, 23, and 26a extend in the direction of axis or plane 38 (as best shown in FIG. 3). However, passage 23 includes walls 25 and 29a which extend in a direction along axis or plane 40 and walls 25b and 29b which extend in a direction along axis of plane 42 (also best shown in FIG. 3). In use, axes 38, 40, and 42 determine the angle of the planar cuts to be made on the bone surface. As such, the angles of axes 38, 40, and 42 can vary depending upon the particular implant to be placed on the bone or the type of surgery being performed. Furthermore, the location of passages 20a, 23, and 26a, in the anterior-posterior direction, on base portion 12 will determine the location of the cuts actually made on the bone surface. In the preferred embodiment, passages 20a, 23, and 26a allow a surgeon to make the typical four cuts on the distal end of the femur, during a total knee arthroplasty.

In a preferred embodiment, saw blade 18 does not contact the various surfaces of base portion 12. Rather, base portion 12 provides the aforementioned passages to allow saw blade 18 to traverse through base portion 12, while working in conjunction with guide portions 14 and 16. As shall be discussed herein, guide portions 14 and 16 provide the support needed to operate saw blade 18. In essence, in the preferred embodiment, base portion 12 is a skeleton that provides spacing and further support to rigid guide portions 14 and 16. However, it is contemplated that base portion 12 can be designed so as to support a cutting tool during resection of the bone surface.

The construction of base or spacer portion 12 does not require a solid piece of polymeric material to be utilized, although such could be utilized. In the preferred embodiment, as best shown in FIG. 4, the molded polymeric base portion 12 has walls 100, 102, 104, 106 around the four sides thereof with bosses 108 molded at the corners thereof. Preferably bosses 108 are threaded after molding. A stiffening rib 110 may be molded on each wall extending from a central portion of each wall generally perpendicular thereto. Flat plate portions 112, 114 are molded adjacent surfaces 100 and 104 and spaced therefrom to provide space for a saw blade 18 to traverse the spacer portion 12. Plate portion 112, 114 may include integrally molded stiffening ribs 116 for rigidity. Two centrally located walls 118, 120 extend inwardly towards the center of base portion 12. Walls 118, 120 are stiffened by a series of ribs 122 which are preferably spaced at regular intervals along each wall forming compartments 124 therebetween. Walls 118 and 120 are spaced at the center of base portion 12 to allow the saw blade to make the chamfer cuts. Preferably the ends of ribs 122 adjacent this central area are tapered inwardly to provide clearance for the saw blade. The taper may be equal to the 45° angle of the champfer cuts. In the preferred embodiment, walls 102 and 106 include integrally molded extensions 52 for receiving optional handles as will be discussed below. Also bone pin holes 126 are preferably molded in each side 102 and 106 to allow for a pair of pins to penetrate base portion 12. Besides making the cutting block lighter, this type of design allows for the further reduction of expenses associated with the construction of base portion 14 and the overall expense of cutting block 10. Such a molding results in less polymeric material being required in the manufacture of base portion 12. However, the design allows base portion 12 to remain rigid enough to provide the proper support required in use of cutting block 10. It is contemplated that the dimensions of base portion 12 can vary. Depending upon the type of cutting tool used, the type or size of implant to be installed, the type or size of bone to be resected, or the dimensions of the other elements of cutting block 10, the dimensions of base portion 12 may vary accordingly. For example, base portion 12 can decrease in size with the increase in size of the other elements of cutting block 10 or can increase in size along with an overall increase in size of cutting block 10 for resecting a larger bone.

Figure 5:
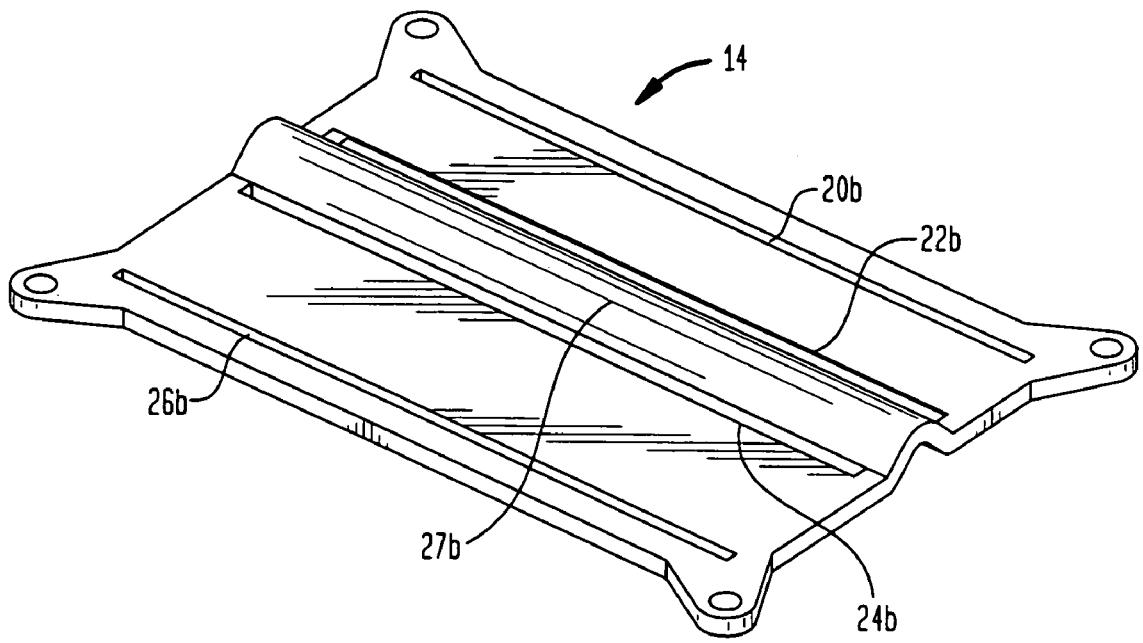
FIG. 5 is a perspective view of a first guide portion according to an embodiment of the present invention, where the guide portion is flipped 180° from that shown in FIGS. 1 and 2.

First guide portion 14 is best shown in FIG. 5. Typically guide portion 14 is constructed of a metal, but can be constructed of any material suitable for properly supporting and guiding saw blade 18. For example, in the preferred embodiment, first guide portion 14 is a plate 0.080 inches thick and constructed of 316 stainless steel (commonly used in medical instruments), but in another embodiment, first guide portion 14 can be constructed of other suitable material. Preferably, the material should be one that produces low friction and wear and can support a saw blade, as well as being relatively inexpensive. Such a stainless steel plate can easily be stamped in large quantities which reduces the cost of manufacturing. However, it is noted that stamping is only one method of manufacturing guide portion 14. Depending upon the thickness of guide portion 14, other methods of manufacturing might be required.

In the preferred embodiment, first guide portion 14 includes passages 20b, 22b, 24b, and 26b extending therethrough (best shown in FIG. 5). While passages 20b and 26b extend in a generally perpendicular direction with respect to the face of first guide portion 14 (i.e. in the direction of axis 38), passages 22b and 24b extend at an angle typically of 45 degrees. However, this angle can vary depending upon the angle of chamfer cuts required. First guide portion 14 also includes section 27b extending between passages 22b and 24b. This section is essentially a triangular section extending from first guide portion 14. Section 27b provides a support surface for saw blade 18 and guides one side of saw blade 18 along either the axis 40 or the axis 42.

Figure 6:
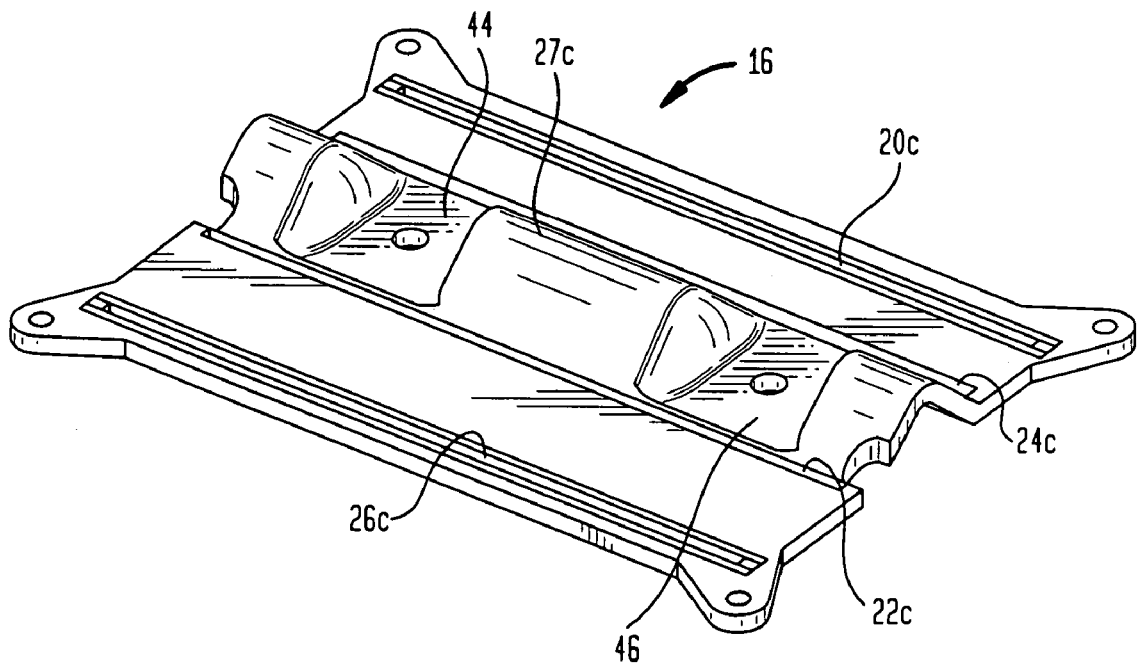
FIG. 6 is a perspective view of a second guide portion according to an embodiment of the present invention.

Second guide portion 16 is shown in FIG. 6 and is similar to first guide portion 14. In the preferred embodiment, the shape and dimensions of second guide portion 16 vary from that of first guide portion 14, while the material utilized is the same. The variation in size and dimension is dictated by the location and angle of cuts to be made. However it is contemplated that other designs for second guide portion 16 can be utilized including a mirror image of first guide portion 14 in both shape and material. In the preferred embodiment, second guide portion 16 includes passages 20c, 22c, 24c, and 26c extending therethrough (best shown in FIG. 6). While passages 20c and 26c extend in a generally perpendicular direction with respect to the face of second guide portion 16 (i.e. in the direction of axis 38), passages 22c and 24c extend at an angle typically of 45 degrees. However, this angle can vary depending upon the angle of chamfer cuts required. Second guide portion 16 also includes section 27c extending between passages 22c and 24c. This section is essentially a triangular section extending from second guide portion 16. Section 27c provides a support for saw blade 18 and guides one side of saw blade 18 along either the axis 40 or the axis 42.

Passages 20c and 26c of second guide portion 16 correspond to passages 20a and 26a of base portion 12 and passages 20b and 26b of first guide portion 14. In operation, the aforementioned passages cooperate with one another so that corresponding passages (e.g. 20a, 20b, and 20c) form one continuous passage (e.g. 20) through cutting block 10. Furthermore, sections 27b and 27c allow for passages 22b and 24b and 22c and 24c, respectively, to correspond with passage 23, thereby forming continuous passage 22 along axis 40 and continuous passage 24 along axis 42. It should be noted that other embodiments are envisioned. For example, passage 23 in base portion 12 could be replaced with two separate passages extending along axes 40 and 42 respectively. In this alternate embodiment, first guide portion 14 would not include section 27b and second guide portion 16 would not include section 27c.

In the preferred embodiment, a fully constructed cutting block 10 (as best shown in FIG. 1) includes first guide portion 14 and second guide portion 16 attached to the opposing faces 13 and 15 of base portion 12. The mode of attachment of first guide portion 14 and second guide portion 16 to base portion 12 can be accomplished in any manner. For example, rivets, pins, screws, or adhesive, as well as many other means for attachment can be utilized. In the preferred embodiment, as shown in FIG. 1, screws 34 extend from first guide portion 14 through base portion 12, and into threaded holes of second guide portion 16. In this mode, base portion 12, first guide portion 14 and second guide portion 16 include extended portions 35 for facilitating connection. However, it is contemplated that other configurations can also be utilized. For example, base portion 12 may include bosses or extensions that insert into guide portions 14 and 16 and retain them in contact with base portion 12. In another embodiment, first and second guide portions 14 and 16 can be molded into the polymer of base portion 12. Finally, base portion 12 may be designed so that guide portions 14 and 16 snap into place. It is also noted that cutting block 10 may include any variation of the elements discussed above.

In the preferred embodiment, the fully constructed cutting block includes four passages 20, 22, 24, and 26 extending therethrough. Each of these passages corresponds to a different cut on the distal end of the femur, matching an implant surface. It is contemplated that cutting block 10 can include any number of passages that correspond to any required cut on any bone surface. For example, cutting block 10 can include only two passages for making only two of the aforementioned four cuts on the distal end of the femur. In the preferred embodiment, the four passages 20, 22, 24, and 26 extending through cutting block 10 include passages 20a, 23, and 26a of base portion 12, 20b, 22b, 24b, and 26b of first guide portion 14, and 20c, 22c, 24c, and 26c of second guide portion 16. Perpendicular passages (i.e. passages 20 and 26) include like passages (e.g. 20a, 20b, and 20c) which correspond with one another to form one continuous passage extending through cutting block 10 (e.g. passage 20), while angled passages (i.e. 22 and 24) include sections 27b and 27c which correspond with like passages (e.g. passages 22b and 22c) and passage 23 to form one continuous passage extending at an angle through cutting block 10 (e.g. passage 22). Each passage accommodates saw blade 18 and guides the same during the cutting of the bone surface. The first guide portion 14 and second guide portion 16 provide the support needed to guide saw blade 18. It is recognized that the metallic composition of these portions allows for better support of the saw blade 18. For this reason, as stated above, first guide portion 14 and second guide portion 16 are constructed from material that is as hard or harder than saw blade 18 and only allows movement within the aforementioned passages.

Cutting block 10 may also include elements for attaching to a bone surface. In the preferred embodiment, locating pins 28 (shown in FIG. 1-3) allow for the fixation of cutting block 10 to the previously resected surface of the distal end of the femur. Locating pins 28 are attached to second guide portion 14 and during use extend therefrom into the bone surface. It is noted that locating pins 28 can either be fixably attached or removably attached to second guide portion 14. In the preferred embodiment, second guide portion 16 includes flat sections 44 and 46 for mounting pins 28. Flat sections 44 and 46 include apertures for receiving pins 28. These apertures can be threaded for removable attachment of pins 28. However, other modes of attachment are contemplated. It is also contemplated that locating pins 28 can be located on any part of cutting block 10, with or without flat sections 44 and 46. Furthermore, locating pins 28 are only one example of a way of attaching cutting block 10 to a bone surface. Another way for attaching the cutting block 10 to a bone surface is by using bone pins 32 extending through holes in cutting block 10

Figure 2:
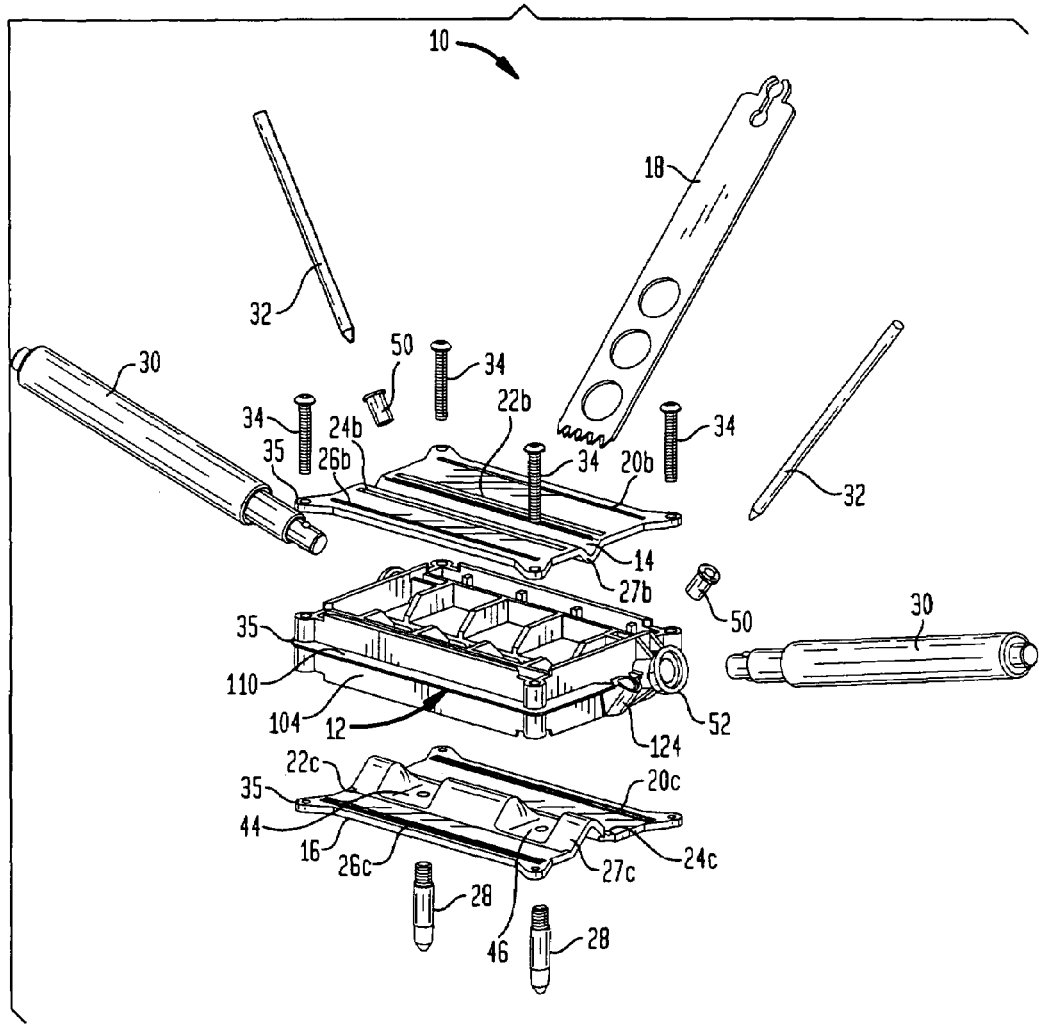
FIG. 2 is an exploded perspective view of the apparatus according to an embodiment of the present invention showing outer metal plates and a molded plastic body.

(shown in FIGS. 1 and 2). Bone pins 32 can be aligned so as to contact the bone surface at an angle from cutting block 10. When bone pins 32 are used, metal bushings 50 (shown in FIG. 2) can be inserted into polymeric portion 12 to provide better support. Additionally, an external support system can be employed to fix cutting block 10 with respect to the bone surface to be resected.

The width of cutting block 10 in the medial-lateral direction of the femur and the height of the cutting block 10 in the anterior-posterior direction of the femur are chosen based on the size of the distal femur being resurfaced and the femoral implant being used. Thus, various sized cutting blocks 10 may be utilized. Cutting block 10 may be aligned on the distal femur in any well known manner, such as by using an intramedulary or extramedulary alignment systems or by computer assisted navigation.

As depicted in FIGS. 1 and 2, the preferred cutting block 10 of one embodiment of present invention includes handles 30. Handles 30 are preferably detachable from cutting block 10, such as by being threaded. It is also contemplated that base portion 12 can include extensions 52 for more easily attaching handles 30. As is known, handles 30 aid in the aligning and fixing of cutting block 10 with respect to the bone surface to be resected. In use, a surgeon grasps handles 30 and guides cutting block 10 into place. Thereafter, cutting block 10 is fixed using any of the means for attaching to a bone surface described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic cutting block for guiding a bone cutting tool to make four cuts on the resected distal end of the femur comprising:

a. a base portion having a first side, a second side, and three passages extending from said first side to said second side, said base portion being made of a polymer material;
   b. a first guide portion having four slots extending through said first guide portion, said first guide portion being made of metal; and
   c. a second guide portion having four slots extending through said second guide portion, said second guide portion being made of metal;
   wherein said first guide portion is attached to said first side of said base portion, said second guide portion is attached to said second side of said base portion, and said three passages of said base portion, said slots on said first guide portion and said second guide portion align to form four passages extending through said cutting block for guiding said bone cutting tool and wherein said base portion is constructed of a different material than said first and second guide portions.

2. The orthopedic cutting block of claim 1, wherein said first or second guide portion further comprises means for attaching to a bone surface.

3. The orthopedic cutting block of claim 2, wherein said means for attaching to a bone surface are pins.

4. A bone cutting block for guiding a bone cutting tool comprising:

a polymeric first body portion having at least three apertures extending therethrough for receiving said bone cutting tool; and
   a non-polymeric second body portion having four cutting tool guide surfaces thereon, said second body portion coupled to said first body portion so that said three apertures and said four cutting guide surfaces are in communication with one another to form four passages adapted to guide said cutting tool.

5. The bone cutting block as set forth in claim 4, wherein said second body portion is constructed of metal.

6. The bone cutting block as set forth in claim 5, wherein said means for attaching to a bone surface are pins.

7. The bone cutting block as set forth in claim 4, further comprising means for attaching to a bone surface.

* * * * *